US010230329B2

(12) United States Patent
Tu et al.

(10) Patent No.: US 10,230,329 B2
(45) **Date of Patent: *Mar. 12, 2019**

(54) PHOTONIC DEGRADATION MONITORING FOR SEMICONDUCTOR DEVICES

(71) Applicant: SUNPOWER CORPORATION, San Jose, CA (US)

(72) Inventors: Xiuwen Tu, San Jose, CA (US); David Aitan Soltz, San Jose, CA (US); Michael C. Johnson, Alameda, CA (US); Seung Bum Rim, Palo Alto, CA (US); Taiqing Qiu, Los Gatos, CA (US); Yu-Chen Shen, Sunnyvale, CA (US); Kieran Mark Tracy, San Jose, CA (US)

(73) Assignee: SunPower Corporation, San Jose, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/425,709

(22) Filed: Feb. 6, 2017

(65) Prior Publication Data

US 2017/0149383 A1 May 25, 2017

Related U.S. Application Data

(63) Continuation of application No. 14/705,268, filed on May 6, 2015, now Pat. No. 9,564,854.

(51) Int. Cl.
*G01N 21/64* (2006.01)
*H02S 50/15* (2014.01)

(52) U.S. Cl.
CPC ......... *H02S 50/15* (2014.12); *G01N 21/6408* (2013.01); *G01N 21/6489* (2013.01);
(Continued)

(58) Field of Classification Search
None
See application file for complete search history.

(56) References Cited

U.S. PATENT DOCUMENTS 8,988,096 B1 3/2015 Naiknaware
2007/0007466 A1 1/2007 Laurent
(Continued)

FOREIGN PATENT DOCUMENTS

CN 103080731 A 5/2013
CN 103558558 A 2/2014
(Continued)

OTHER PUBLICATIONS

Second Office Action issued by the Taiwanese Patent Office for Taiwan Patent Application No. 105113953 dated Apr. 26, 2018, 13 pgs.

(Continued)

*Primary Examiner* — Yara B Green
(74) *Attorney, Agent, or Firm* — Schwabe, Williamson & Wyatt, P.C.

(57) ABSTRACT

Methods of testing a semiconductor, and semiconductor testing apparatus, are described. In an example, a method for testing a semiconductor can include applying light on the semiconductor to induce photonic degradation. The method can also include receiving a photoluminescence measurement induced from the applied light from the semiconductor and monitoring the photonic degradation of the semiconductor from the photoluminescence measurement.

20 Claims, 4 Drawing Sheets

START

APPLYING LIGHT TO A SEMICONDUCTOR TO INDUCE DEGRADATION — 100

RECEIVING A PHOTOLUMINESCENCE MEASUREMENT INDUCED FROM THE APPLIED LIGHT FROM THE SEMICONDUCTOR — 102

MONITORING THE DEGRADATION OF THE SEMICONDUCTOR BASED ON THE PHOTOLUMINESCENCE MEASUREMENT — 104

END

(52) U.S. Cl.
CPC ................ *G01N 2201/0621* (2013.01); *G01N 2201/06113* (2013.01)

(56) References Cited

U.S. PATENT DOCUMENTS

| | | | |
|---|---|---|---|
| 2007/0008518 | A1 | 1/2007 | Hummel et al. |
| 2009/0206287 | A1 | 8/2009 | Trupke et al. |
| 2011/0025839 | A1 | 2/2011 | Trupke et al. |
| 2011/0180688 | A1 | 7/2011 | Nakahara |
| 2011/0220194 | A1 | 9/2011 | Kurtin et al. |
| 2012/0012756 | A1 | 1/2012 | Beck et al. |
| 2012/0025100 | A1 | 2/2012 | Allenic et al. |
| 2012/0248335 | A1 | 10/2012 | Kim et al. |
| 2014/0084180 | A1 | 3/2014 | Li et al. |
| 2014/0319317 | A1 | 10/2014 | Lai et al. |
| 2015/0155829 | A1 | 6/2015 | Stoicescu et al. |

FOREIGN PATENT DOCUMENTS

| | | | |
|---|---|---|---|
| JP | 2016180242 | A | 10/2016 |
| TW | 201424030 | A | 6/2014 |
| WO | 2007098021 | A2 | 8/2007 |
| WO | WO-2011017775 | | 2/2011 |

OTHER PUBLICATIONS

International Preliminary Report on Patentability from PCT/US2016/030476 dated Nov. 16, 2017, 12 pgs.

Sopori, et al., "Understanding Light-Induced Degradation of c-Si Solar Cells" 2012 IEEE Photovoltaic Specialists Conference, Austin, Texas, Jun. 3-8, 2012, 8 pgs.

International Search Report and Written Opinion for PCT Patent Application No. PCT/US2016/030476 dated Aug. 9, 2016, 15 pgs.

PHOTONIC DEGRADATION MONITORING FOR SEMICONDUCTOR DEVICES

CROSS-REFERENCE TO RELATED APPLICATIONS

This application is a continuation of U.S. patent application Ser. No. 14/705,268, filed on May 6, 2015, the entire contents of which are hereby incorporated by reference herein.

BACKGROUND

Semiconductor devices, for example photovoltaic (PV) cells among others, are well known electronic devices. In one example, photovoltaic (PV) cells, commonly known as solar cells, are devices for conversion of solar radiation into electrical energy. Generally, solar radiation impinging on the surface of, and entering into, the substrate of a solar cell creates electron and hole pairs in the bulk of the substrate. The electrons and holes migrate to p-doped and n-doped regions in the substrate, respectively, thereby creating a voltage differential between the doped regions. The doped regions are connected to the conductive regions on the solar cell to direct an electrical current from the cell to an external circuit.

DETAILED DESCRIPTION

Figure 1:
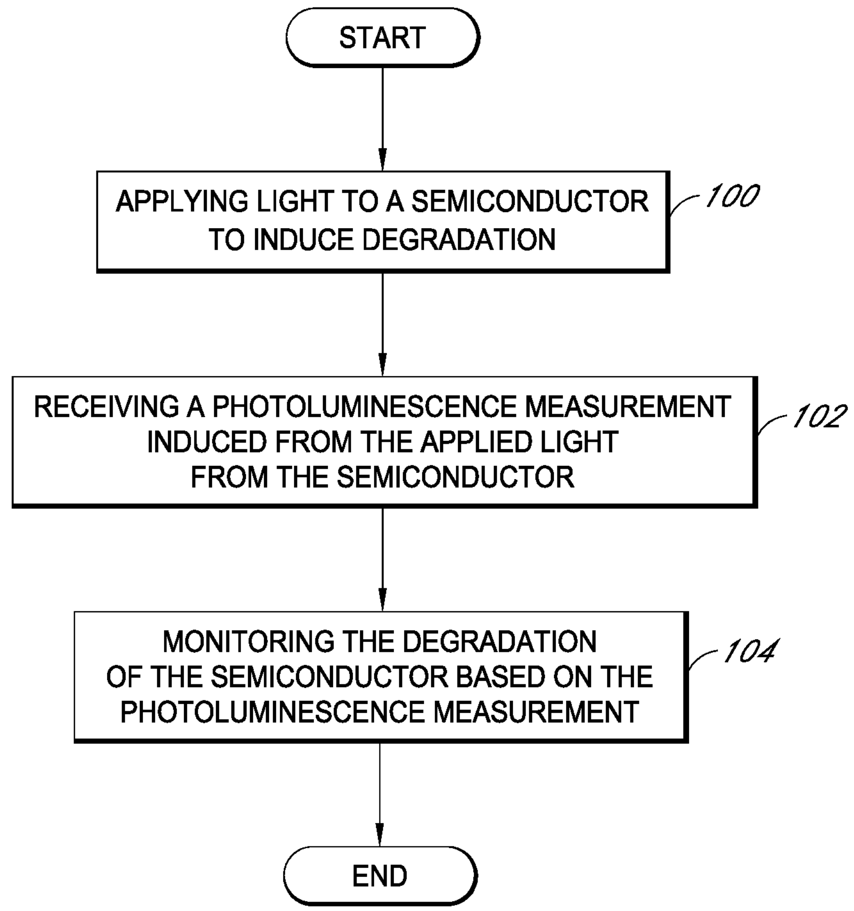
FIG. 1 illustrates a flow chart representation of a method for testing a semiconductor, according to some embodiments

The following detailed description is merely illustrative in nature and is not intended to limit the embodiments of the subject matter of the application or uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

This specification includes references to "one embodiment" or "an embodiment." The appearances of the phrases "in one embodiment" or "in an embodiment" do not necessarily refer to the same embodiment. Particular features, structures, or characteristics may be combined in any suitable manner consistent with this disclosure.

Terminology. The following paragraphs provide definitions and/or context for terms found in this disclosure (including the appended claims):

"Comprising." This term is open-ended. As used in the appended claims, this term does not foreclose additional structure or steps.

"Configured To." Various units or components may be described or claimed as "configured to" perform a task or tasks. In such contexts, "configured to" is used to connote structure by indicating that the units/components include structure that performs those task or tasks during operation. As such, the unit/component can be said to be configured to perform the task even when the specified unit/component is not currently operational (e.g., is not on/active). Reciting that a unit/circuit/component is "configured to" perform one or more tasks is expressly intended not to invoke 35 U.S.C. § 112, sixth paragraph, for that unit/component.

"First," "Second," etc. As used herein, these terms are used as labels for nouns that they precede, and do not imply any type of ordering (e.g., spatial, temporal, logical, etc.). For example, reference to a "first" semiconductor does not necessarily imply that this semiconductor is the first semiconductor in a sequence; instead the term "first" is used to differentiate this semiconductor from another semiconductor (e.g., a "second" semiconductor). In an example semiconductors can include silicon substrates and/or photovoltaic devices such as solar cells among other examples. In one example, a "semiconductor" testing apparatus can be a solar cell testing apparatus.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

"Coupled"—The following description refers to elements or nodes or features being "coupled" together. As used herein, unless expressly stated otherwise, "coupled" means that one element/node/feature is directly or indirectly joined to (or directly or indirectly communicates with) another element/node/feature, and not necessarily mechanically.

"Inhibit"—As used herein, inhibit is used to describe a reducing or minimizing effect. When a component or feature is described as inhibiting an action, motion, or condition it may completely prevent the result or outcome or future state completely. Additionally, "inhibit" can also refer to a reduction or lessening of the outcome, performance, and/or effect which might otherwise occur. Accordingly, when a component, element, or feature is referred to as inhibiting a result or state, it need not completely prevent or eliminate the result or state.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import.

In the following description, numerous specific details are set forth, such as specific operations, in order to provide a thorough understanding of embodiments of the present disclosure. It will be apparent to one skilled in the art that embodiments of the present disclosure may be practiced without these specific details. In other instances, well-known techniques are not described in detail in order to not unnecessarily obscure embodiments of the present disclosure.

The capability to measure degradation in an accelerated manner can be crucial to improving a semiconductor product performance and reliability of the product in the field. For example, photonic induced degradation (e.g., degradation from specific wavelengths of light) can deteriorate the performance of a semiconductor over time. In a specific example, ultraviolet (UV) induced degradation can deteriorate the performance of a solar cell out in the field. Thus, specific test methods are desirable to determine if solar cells are susceptible to ultraviolet (UV) induced degradation during manufacture or prior to product shipment to prevent product which is susceptible to ultraviolet (UV) induced degradation from reaching the customer or installation in the field. The longevity of a solar cell and/or solar cell module can directly affect the value of the product to a customer and the product's competitiveness in the marketplace. Also, the rapid pace of semiconductor process development and qualification can require a high acceleration factor (AF), e.g., to have test results available in a timely manner for use and/or feedback to the semiconductor manufacturing process.

This specification describes example methods for testing a semiconductor, followed by example semiconductor testing apparatus. For ease of understanding, much of the specification describes testing of solar cells. The described techniques and structures can apply outside of context of solar cells, for example, to semiconductor devices more generally. Various examples are provided throughout.

Turning now to FIG. 1, a flow chart illustrating a method for testing a semiconductor is shown, according to some embodiments. In various embodiments, the method of FIG. 1 can include additional (or fewer) blocks than illustrated. In an example, a passivation region can be formed on the semiconductor substrate prior to applying the light at 100 below.

At 100, light can be applied to a semiconductor to induce degradation. In one embodiment, light can be applied to a solar cell to induce photonic degradation. In an embodiment, the light can be in the range of one or more wavelength groups shown in Table 1 below.

TABLE 1

Example Wavelength Groups

| Wavelength Groups | Wavelength Range | Wavelength Range |
|---|---|---|
| 1 | 101-280 nm | UVC |
| 2 | 280-315 nm | UVB |
| 3 | 315-400 nm | UVA |
| 4 | 400-500 nm | Visible |
| 5 | 500-600 nm | |
| 6 | 600-700 nm | |
| 7 | 700-800 nm | Near IR |
| 8 | 800-900 nm | |
| 9 | 900-1000 nm | |

In an embodiment, light from specific wavelength groups (groups 1-9 from Table 1) can be applied to a semiconductor to induce specific modes of degradation to the semiconductor and/or solar cell, with respect to the chosen wavelength group. As shown, wavelength groups 1-3 correspond to the ultraviolet (UVA-UVC) wavelength range, wavelength groups 4-6 correspond to the visible range and the wavelength groups 7-9 correspond to the near infrared (IR) wavelength range. In an example, degradation from ultraviolet (UV) light (e.g., one or more of groups 1-3 of Table 1) is one mode of degradation, among others, which can affect the overall solar cell performance and reliability over time. Thus, specific test methods are desirable to determine if solar cells are susceptible to ultraviolet (UV) degradation during manufacture or prior to product shipment. These test methods can be very useful in preventing product which is susceptible to ultraviolet (UV) degradation from reaching the customer or installation in the field.

Using a broadband source of light, such as a mercury lamp, has the disadvantage of exposing the solar cell to a broad spectrum of light. In an example, a mercury lamp can emit irradiance in the ultraviolet (UV), visible, and infrared (IR) spectral range. Also, the amount of ultraviolet (UV) light emitted by the mercury lamp can be limited. In one example, long exposure times from a mercury lamp are required to induce similar ultraviolet (UV) degradation a solar cell would undergo from ultraviolet (UV) light exposure in the field. In addition, the spectrum of the mercury lamp contains many spikes and the intensities of these spikes are known to vary, either from lamp to lamp or over time. Such variations can be a source of inconsistency and/or uncertainty for use in ultraviolet (UV) testing.

Although applying ultraviolet (UV) light to induce ultraviolet (UV) degradation is mentioned herein, other light sources and degradation modes can be applied and/or induced with the discussed methods described.

In an embodiment, the applied light can have photon energy that is greater than the bandgap energy of the semiconductor. In one embodiment, the applied light can have a wavelength that is shorter than the wavelength corresponding to the semiconductor band gap energy. In an example, the semiconductor can be a silicon substrate and/or a solar cell. In an embodiment, a laser and/or a light emitting diode (LED) can be used as a light source. In an embodiment, although example wavelength groups (e.g., light in the range of 100-1000 nm) are discussed, light having above 1000 nm wavelength can be used. In an embodiment, ultraviolet (UV) light (e.g., one or more of groups 1-3 of Table 1), can be used to induce ultraviolet (UV) degradation to the solar cell. In an embodiment, light having a wavelength in the range of 100-1000 nm can be used.

In an embodiment, using light from a narrowband source (e.g., using a laser or a light emitting diode (LED) allows for reduced exposure times in comparison to using light from a broadband source (e.g., using mercury lamps can take several days and/or weeks). In an embodiment, a narrowband source can include one or more of the wavelength groups 1-9 of Table 1. In an embodiment, the light can be applied for less than a second to induce degradation on the semiconductor. In one embodiment, the light can be applied to the semiconductor up to 1-2 hours or more to induce photonic degradation. In an embodiment, light can be applied to the semiconductor for a duration in the range of 10 milliseconds-2 hours to induce photonic degradation.

Figure 5:
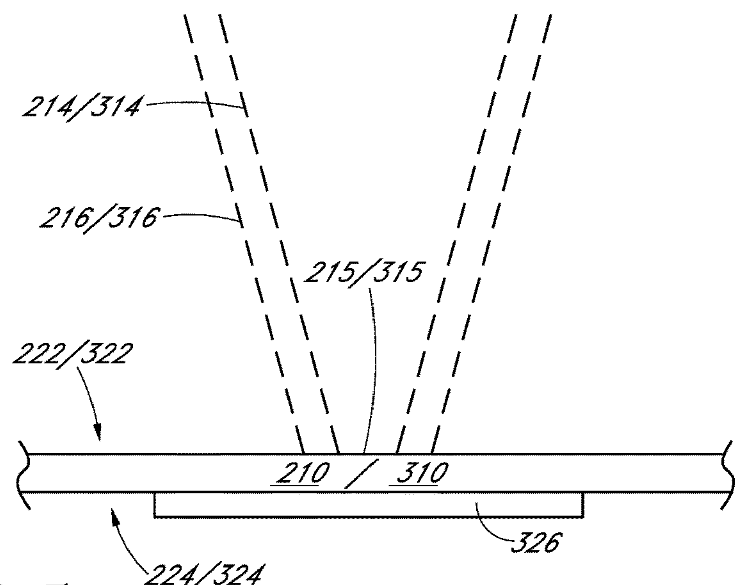
FIG. 5 illustrates a cross-sectional view of applying light to a semiconductor, according to some embodiments.

In an embodiment, the light can be applied on a passivation region of the semiconductor. For example, such a passivation region can be an anti-reflective region (AR) of the solar cell. In an embodiment, the passivation region can be on a front side and/or a back side of the solar cell. In one example, the light can be applied to a passivation region on the front side of the solar cell opposite to a contact region on a back side of the solar cell (e.g., as shown in FIG. 5). In an embodiment, the light can be applied to one or more locations of the solar cell. In an example, the light can be applied to one or more locations on the front side of the solar cell opposite to one or more contact regions (e.g., a first contact pad, second contact pad, etc.) on a back side of the solar cell (as shown in FIG. 5).

Figure 6:
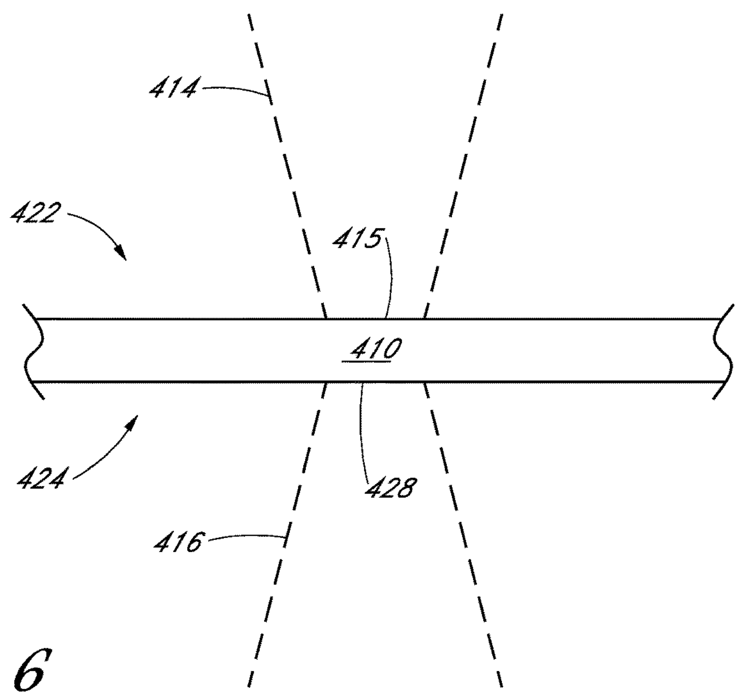
FIG. 6 illustrates another cross-sectional view of applying light to a semiconductor, according to some embodiments.

At 102, a photoluminescence measurement induced from the applied light can be received from the semiconductor. In one embodiment, the photoluminescence measurement induced from the applied light can be received from a location of the semiconductor. In an embodiment, a photoluminescence intensity can be used to measure the photoluminescence at the semiconductor. In an embodiment, the photoluminescence measurement can be received from a front side and/or a back side of the semiconductor (as shown in FIGS. 5 and 6). In one embodiment, the photoluminescence measurement can be indicative of degradation at a front side and/or a back side of the semiconductor.

In an embodiment, the method can be performed at multiple locations of the semiconductor to induce degradation at multiple locations of the semiconductor and receive multiple corresponding photoluminescence measurements. In an example, the light can be applied to a plurality of locations on a front side of the solar cell opposite to a plurality of contact pads (e.g., a first contact pad, second contact pad, etc.) on a back side of the solar cell, and a corresponding induced photoluminescence measurements can be received. In an embodiment, a plurality of photoluminescence measurement can be used to generate a map, (e.g., a photonic degradation map) or other indicator of the degradation on the semiconductor.

At 104, degradation of the semiconductor can be monitored based on the photoluminescence measurement, according to some embodiments. In one embodiment, photonic degradation of a solar cell can be monitored based on the photoluminescence measurement. In an embodiment, the monitoring can include receiving a first photoluminescence measurement induced from an applied light and receiving a second photoluminescence measurement induced from the applied light (e.g., light from the same source) after receiving the first photoluminescence measurement.

In an example, light illuminating a solar cell can generate electron and hole pairs. At steady state, the density of the generated electron and hole pairs depend on the passivation of the solar cell. Under equal illumination, for a solar cell with good passivation (e.g., low surface recombination), the higher the generated electron and hole density, the higher the photoluminescence intensity. In an embodiment, reduced photoluminescence intensity can indicate degradation in a passivation region (e.g., silicon dioxide and/or silicon nitride) of the solar cell. Thus, monitoring the measured change of the photoluminescence intensity under constant illumination can determine the change in a passivation (e.g., induced degradation) of a solar cell. In one embodiment, the surface recombination of the solar cell can be measured using the photoluminescence intensity.

In an example, ultraviolet (UV) light can be used to induce ultraviolet (UV) degradation to a solar cell. In the same example, the applied ultraviolet (UV) light can induce a corresponding photoluminescence which can be measured to monitor the ultraviolet (UV) induced degradation to the solar cell. In one embodiment, the ultraviolet (UV) light can be applied for a duration in the range of 10 milliseconds-2 hours to induce photonic ultraviolet (UV) degradation. In an embodiment, the ultraviolet (UV) light can be applied from a laser or a light emitting diode (LED). In an embodiment, ultraviolet (UV) light can be applied to a first location of the solar cell to induce ultraviolet (UV) degradation at the first location. In an embodiment, a first photoluminescence, induced from the ultraviolet (UV) light, can be measured to monitor the ultraviolet (UV) induced degradation to the solar cell. In one embodiment, the monitoring can include receiving a first photoluminescence measurement induced from the ultraviolet (UV) light and receiving a second photoluminescence measurement induced from the ultraviolet (UV) light after the first photoluminescence measurement. In an embodiment, the ultraviolet (UV) light can be applied to a location on a front side of the solar cell opposite to a contact pad of a solar cell and an induced photoluminescence measurement can be received. In an embodiment, the ultraviolet (UV) light can be applied to a passivation region of a solar cell to induce ultraviolet (UV) degradation at the passivation region.

In an embodiment, ultraviolet (UV) light can be applied to multiple locations (e.g., first location, second location, etc.) of the solar cell to induce ultraviolet (UV) degradation at multiple locations of the solar cell. In the same example, multiple photoluminescence measurements (e.g., a first photoluminescence, second photoluminescence, etc.), induced from the ultraviolet (UV) light, can be measured to monitor the ultraviolet (UV) induced degradation to the solar cell. In one example, the ultraviolet (UV) light can be applied to a plurality of regions on the front side of the solar cell corresponding to contact pads (e.g., a first contact pad, second contact pad, etc.) on the back side of the solar cell, and a plurality of induced photoluminescence measurements can be received. In an embodiment, the plurality of photoluminescence measurements can be used to generate a map, (e.g., a photonic degradation map) or other indicator of the ultraviolet (UV) induced degradation to the solar cell. In one embodiment, the monitoring can include receiving a plurality of photoluminescence measurements induced from the applied ultraviolet (UV) light and mapping the ultraviolet (UV) induced degradation at the plurality of locations of the solar cell to the photonic degradation map. In an embodiment, the induced photonic degradation to the solar cell can be monitored based on the photonic degradation map.

In an example, ultraviolet (UV) light can be applied to a first location of the solar cell to induce ultraviolet (UV) degradation at the first location and a first and second photoluminescence measurement induced from the applied ultraviolet (UV) light can be received. In the same example, ultraviolet (UV) light can be applied to a second location of the solar cell to induce ultraviolet (UV) degradation at the second location and a third and fourth photoluminescence measurement induced from the applied ultraviolet (UV) light can be received. In the same example, ultraviolet (UV) induced degradation of the solar cell can be monitored from the first, second, third and fourth photoluminescence measurements.

In an embodiment, the method of FIG. 1 can be performed on a solar cell during its manufacture. In an example, within a solar cell manufacturing process, the method of FIG. 1 can be performed following the formation of a passivation region (e.g., silicon dioxide and/or silicon nitride) on a semiconductor substrate. In one embodiment, the method of FIG. 1 can be performed on a solar cell after manufacture, e.g. on a finished product, such as a solar cell or module. Some advantages to the method of FIG. 1 over other methods can include an improved acceleration factor (AF), e.g., test results can be made available for use and/or feedback to the semiconductor process in-line in a matter of minutes and/or hours as compared to other methods which can take days and/or weeks.

In an embodiment, steps 100, 102 and 104 can be performed in the same process. In an embodiment, the steps 100, 102 and 104 can be performed sequentially (e.g., performing 100, 102 and then 104) and/or simultaneously. In one example, during the application of light, a photoluminescence measurement can be received and the degradation monitored from photoluminescence measurement. In an example, light can be applied for 1 second, a photoluminescence measurement received after applying the light and the degradation monitored from the photoluminescence measurement received. In an embodiment, other test methods can be combined with the method of FIG. 1 (e.g., hot spot testing, etc.).

Figure 2:
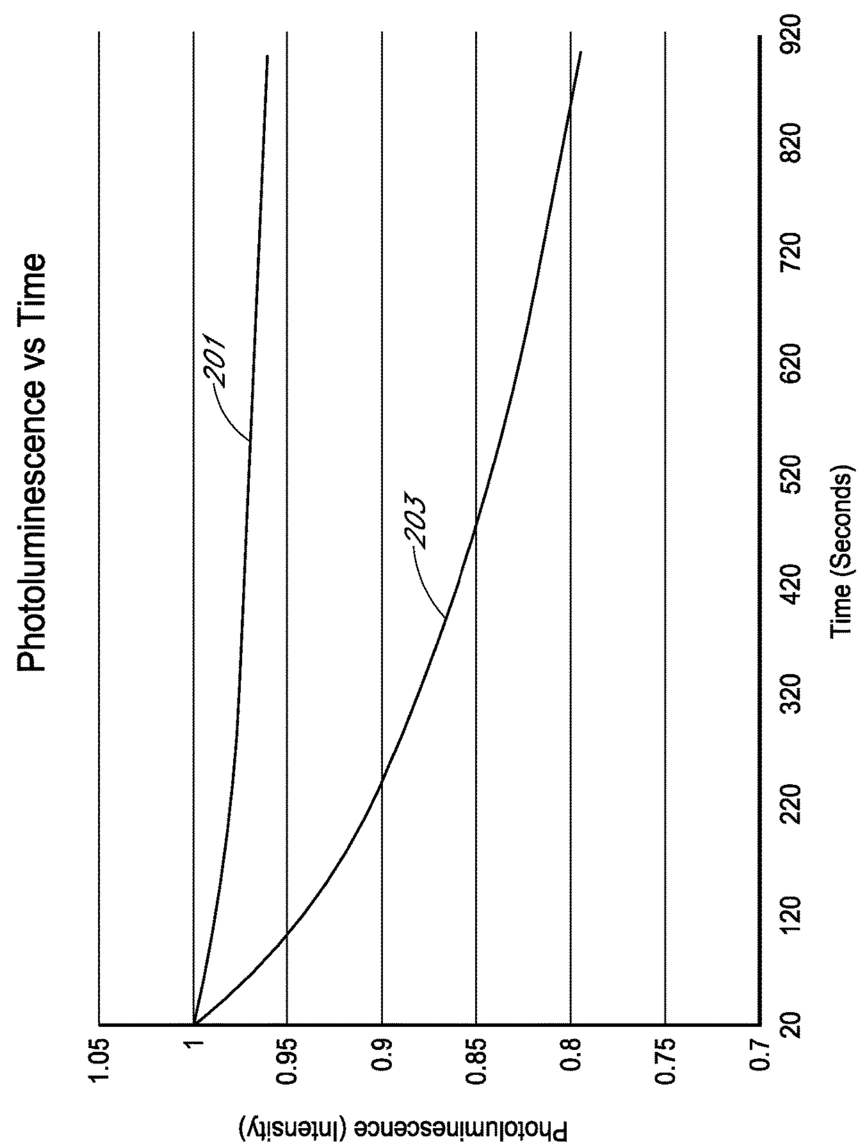
FIG. 2 illustrates example data for photoluminescence vs time, according to some embodiments.

FIG. 2 illustrates example data for photoluminescence vs time, according to some embodiments. As shown, the photoluminescence data is normalized to simplify presentation of the data.

In particular, two photoluminescence measurements, 201 and 203 are shown in FIG. 2. In the example shown, the measurements are performed during exposure to ultraviolet (UV) light. In another example, the measurements can be performed after applying ultraviolet (UV) light. As shown, measurement 203 illustrates an approximately 20% reduction in photoluminescence over time (e.g., over 900 seconds). Measurement 201 shows less than 5% reduction in the photoluminescence measurement over the same duration. In the example shown, a deterioration, e.g., greater than 5% photoluminescence loss can be defined as a no go and the ultraviolet (UV) degradation of that solar cell determined to be unacceptable. Thus, in the same example, measurement 201 can be acceptable (passing solar cell) and measurement 203 can correspond to a failing solar cell. Although one example is presented herein, other example configurations and/or measurements may be used.

Figure 3:
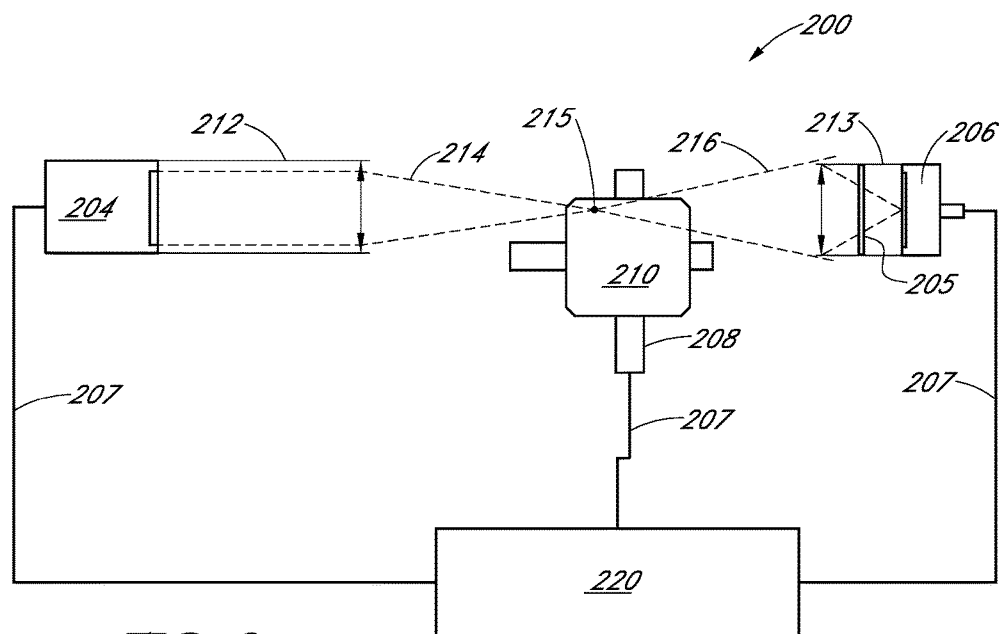
FIG. 3 illustrates a schematic top down view of a semiconductor testing apparatus, according to some embodiments.

With reference to FIG. 3, an example semiconductor testing apparatus is shown, according to some embodiments. In one embodiment, the semiconductor testing apparatus 200 is configured to test a semiconductor 210. In an embodiment, the semiconductor 210 can be a solar cell. In an embodiment, the semiconductor 210 can have a front side opposite a back side of the semiconductor 210. In an embodiment, the semiconductor 210 can be placed on a receiving medium 208. In an example, the receiving medium 208 is an electronic scanning and/or translator stage. In an embodiment, the semiconductor testing apparatus 200 can include a light source 204, where the light source 204 can have an optical tube 212 to focus light 214 from the light source 204 onto a location 215 of the semiconductor 210. In an embodiment, a photoluminescence measurement 216 induced from the applied light 214 can be received from the semiconductor 210. In an embodiment, the photoluminescence measurement 216 can be received from the same location 215 as that focused on by the light 214 (e.g., as shown in FIG. 5). In an embodiment, the location 215 can be on the front side and/or back side of the semiconductor 210. In one embodiment, the light source 204 can be a laser or a light emitting diode (LED). In an embodiment, a light source can be configured to induce photonic degradation to a semiconductor 210. In an example, a narrowband light source can be configured to induce photonic degradation to a solar cell, where the inducing includes applying light to the solar cell. In an embodiment, a detector 206 can be used to receive the photoluminescence measurement 216 from the semiconductor 210. In an embodiment, the detector 206 can be configured to receive the measured photoluminescence 216 induced from the applied light 214. In an embodiment, the detector 206 can also have an optical tube 213 to collect the photoluminescence measurement 216. In one embodiment, a filter 205 can be used to filter out noise from the photoluminescence 216.

In an embodiment, an electronic system 220 can be connected 207 to the light source 204, detector 206 and the receiving medium 208. In an embodiment the electronic system 220 can be used to modulate the light 214 from the light source 204. In an embodiment, the electronic system 220 can be used to monitor the photoluminescence measurement 216 received at the detector 206 and record the photoluminescence measurement 216. In an embodiment, the electronic system 220 can be configured to monitor photonic degradation of a semiconductor from the photoluminescence measurement 216. In an embodiment, the electronic system 220 can be configured to determine whether to pass or fail a semiconductor based on the monitoring. In an embodiment, the electronic system 220 can be used to control the movement of the receiving medium 208 (e.g., a scanning stage). In some embodiments, the light 214 can be scanned along the surface of the semiconductor 210. In an embodiment, the light 214 can be scanned along the front side and/or back side of the semiconductor 210.

In an example, the receiving medium 208 (e.g., a scanning stage) can be used to move the location 215 from one location to another location on the semiconductor 210. In one example, the light 214 can be scanned from one location on the semiconductor to another location using galvanometric scanners. In an embodiment, a plurality of photoluminescence measurements received from scanning from one location to another location on the semiconductor can be used to generate a map, (e.g., a photonic degradation map) or other indicator of the degradation of the semiconductor.

In one embodiment, the electronic system 220 can include an analog to digital converter (ADC), a current amplifier or pre-amplifier to boost, or a picoammeter to read the signal from the photoluminescence measurement. In an embodiment, the electronic system 220 can include an electronic control system to control the light from the light source 204 and/or to control the movement of the receiving medium 208 (e.g., a scanning stage). In some embodiments, other electronics and/or software can be incorporated into the electronic system 220.

Various components of the electronic system and/or one or more portions of the disclosed techniques can be implemented by a processor unit executing program instructions stored on a memory. In various embodiments, the processor unit can include one or more processors or cores. The processor unit can contain a cache or other form of on-board memory. The memory is usable by the processor unit (e.g., to store instructions executable by and data used by the processor unit). The memory can be implemented by any suitable type of physical memory media, including hard disk storage, floppy disk storage, removable disk storage, flash memory, random access memory (RAM-SRAM, EDO RAM, SDRAM, DDR SDRAM, Rambus® RAM, etc.), ROM (PROM, EEPROM, etc.), and so on. The memory can consist solely of volatile memory in one embodiment.

The circuitry can include an I/O interface configured to couple to and communicate with other devices (e.g., to receive a value representing the threshold voltage), according to various embodiments.

Articles of manufacture that store instructions (and, optionally, data) executable by a computer system to implement various techniques disclosed herein are also contemplated. These articles of manufacture include tangible computer-readable memory media. The contemplated tangible computer-readable memory media include portions of the memory subsystem of a computer system (without limitation SDRAM, DDR SDRAM, RDRAM, SRAM, flash memory, and various types of ROM, etc.), as well as storage media or memory media such as magnetic (e.g., disk) or optical media (e.g., CD, DVD, and related technologies, etc.). The tangible computer-readable memory media may be either volatile or nonvolatile memory.

Figure 4:
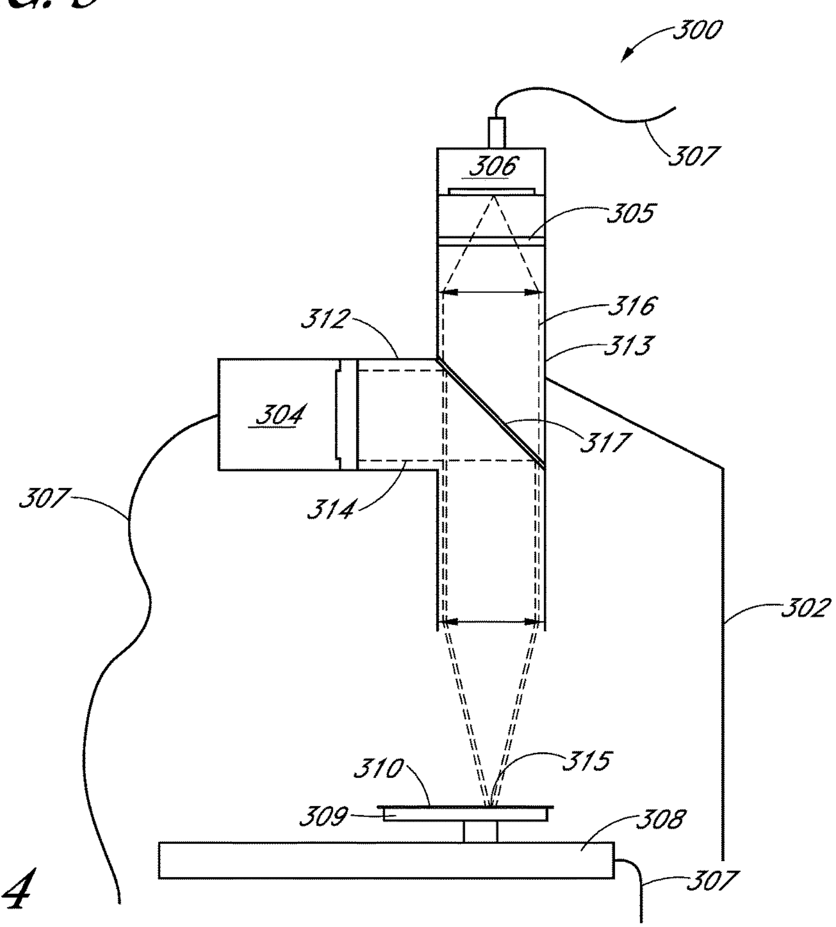
FIG. 4 illustrates a schematic plan view of another semiconductor testing apparatus, according to some embodiments.

FIG. 4 illustrates another example semiconductor testing apparatus, according to some embodiments. As shown, the semiconductor testing apparatus 300 of FIG. 4 has similar reference numbers to elements of FIG. 3, wherein like reference numbers refer to similar elements throughout the figures.

In one embodiment, the semiconductor testing apparatus 300 is configured to test a semiconductor 310. In an embodiment, the semiconductor 310 can be a solar cell. In an embodiment, the semiconductor 310 can have a front side opposite a back side of the semiconductor 310. In an embodiment, the semiconductor testing apparatus 300 can include a light source 304, the light source 304 can have an optical tube 312 to focus light 314 from the light source 304 onto a location 315 of the semiconductor 310. In an embodiment, a photoluminescence measurement 316 induced from the applied light 314 can be received from the semiconductor 310. In an embodiment, the photoluminescence measurement 316 can be received from the same location 315 as that focused on by the light 314 (e.g., as shown in FIG. 5). In an embodiment, the location 315 can be on the front side and/or back side of the semiconductor 310. In one embodiment, the light source 304 can be a laser or a light emitting diode (LED). In an embodiment, a detector 306 can be used to receive the photoluminescence measurement 316 from the semiconductor 310. In an embodiment, the light 314 can be co-axial, e.g., be in the same optical axis, as that of the photoluminescence measurement 316 as shown in FIG. 4. In an example, light from a narrowband light source and the measured photoluminescence 316 can be at least partially co-axial. In an embodiment, a dichroic mirror 317 can be used to separate the light 314 and the photoluminescence measurement 316. In one example, the dichroic mirror 317 can be used to separate light from a narrowband light source (e.g., light from one or more wavelength groups of Table 1) and the measured photoluminescence 316. In an embodiment, the detector 306 can also have an optical tube 313 to collect the photoluminescence measurement 316. In one embodiment, a filter 305 can be used to filter out the source illumination (e.g., light 314) and/or background noise from the photoluminescence measurement 316.

An electronic system, similar to that discussed in FIG. 3, can be connected 307 to the light source 304, detector 306 and receiving medium 308. In an embodiment, the electronic system, not shown, can be used to modulate the light 314 from the light source 304. In an embodiment, the electronic system can be used to monitor the photoluminescence measurement 316 received at the detector 306 and record the photoluminescence measurement 316. In an embodiment, the electronic system can be configured to monitor photonic degradation of a semiconductor from the photoluminescence measurement 316. In an embodiment, the electronic system can be configured to determine whether to pass or fail a semiconductor based on the monitoring. In an embodiment, the photoluminescence measurement 316 can be used to determine the induced degradation to semiconductor 310 (e.g., as discussed in the example of FIG. 2). In an embodiment, the electronic system can be used to control the movement of the receiving medium (e.g., a scanning stage) 308. In an example, the receiving medium 308 is an electronic scanning and/or translator stage. In an embodiment, the receiving medium 308 can also include a chuck 309, where the semiconductor 310 is placed on the chuck 309. In an embodiment, the front and/or back side of the semiconductor 310 can be in contact with the chuck 309. In an embodiment, a mount 302 can hold up the semiconductor testing apparatus 300. In some embodiments, the light 314 can be scanned along the surface of the semiconductor 310. In an embodiment, the light 314 can be scanned along the front side and/or back side of the semiconductor 310.

In an example, the receiving medium 308 (e.g., a scanning stage) can be used to move the location 315 from one location to another location on the semiconductor 310. In one example, the light 314 can be scanned from one location on the semiconductor to another location using galvanometric scanners. In an embodiment, a plurality of photoluminescence measurements received from scanning from one location to another location on the semiconductor can be used to generate a map, (e.g., a photonic degradation map) or other indicator of the degradation of the semiconductor.

As discussed above, various components of the electronic system and/or one or more portions of the disclosed techniques can be implemented by a processor unit executing program instructions stored on a memory. In various embodiments, the processor unit can include one or more processors or cores. The processor unit can contain a cache or other form of on-board memory. The memory is usable by the processor unit (e.g., to store instructions executable by and data used by the processor unit). The memory can be implemented by any suitable type of physical memory media, including hard disk storage, floppy disk storage, removable disk storage, flash memory, random access memory (RAM-SRAM, EDO RAM, SDRAM, DDR SDRAM, Rambus® RAM, etc.), ROM (PROM, EEPROM, etc.), and so on. The memory can consist solely of volatile memory in one embodiment.

The circuitry can include an I/O interface configured to couple to and communicate with other devices (e.g., to receive a value representing the threshold voltage), according to various embodiments.

Articles of manufacture that store instructions (and, optionally, data) executable by a computer system to implement various techniques disclosed herein are also contemplated. These articles of manufacture include tangible computer-readable memory media. The contemplated tangible computer-readable memory media include portions of the memory subsystem of a computer system (without limitation SDRAM, DDR SDRAM, RDRAM, SRAM, flash memory, and various types of ROM, etc.), as well as storage media or memory media such as magnetic (e.g., disk) or optical media (e.g., CD, DVD, and related technologies, etc.). The tangible computer-readable memory media may be either volatile or nonvolatile memory.

With reference to FIG. 5, an example of applying light to a semiconductor to induce degradation is shown, according to some embodiments. In an embodiment, the semiconductor 210/310 can have a front side 222/322 opposite a back side 224/324. In an embodiment, the semiconductor 210/310 can be a solar cell. In an embodiment, light 214/314 can be applied to a location 215/315 of a semiconductor 210 to induce a photoluminescence 216/316, where a photoluminescence measurement 316 can be received from the location 215/315 (e.g., the same location the light 214/314 is applied). In an embodiment, the location 215/315 is on a front side 222/322 of the semiconductor 210/310. In an embodiment, the location 215/315 can be opposite to a contact region 326 on a back side 224/324 of the semiconductor 210/310. In an example, the contact region 326 can be a contact pad. In one embodiment, the location 215/315 can be a passivation region (e.g., silicon dioxide and/or silicon nitride) of a solar cell. As shown, FIG. 5 has similar reference numbers to elements of FIGS. 3 and 4, wherein like reference numbers refer to similar elements throughout the figures.

FIG. 6 illustrates another example of applying light to a semiconductor to induce degradation, according to some embodiments. In an embodiment, the semiconductor 410 can have a front side 422 opposite a back side 424. In an embodiment, the semiconductor 410 can be a solar cell. In an embodiment, light 414 can be applied to a location 415 on a front side 422 of a semiconductor 410 to induce a photoluminescence 416, where a photoluminescence measurement 416 can be received from another location 428 on the back side 424 of the semiconductor 410. In one embodiment, the location 415 can be a passivation region (e.g., silicon dioxide and/or silicon nitride) of a solar cell.

In one embodiment, a light source can be facing the front side 422 to apply light 414 to the front side 422 of the semiconductor 410 and a detector can be facing the back side 424 to receive a photoluminescence measurement from the back side 424 of the semiconductor 410. In an example, a testing apparatus, similar to the testing apparatus of FIGS. 3 and 4, can be used where the testing apparatus can include the light source and detector described in FIG. 6.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A solar cell testing apparatus, comprising:

a narrowband light source configured to induce photonic degradation to a solar cell, wherein the inducing includes applying light to the solar cell;

a detector configured to measure photoluminescence induced from the applied light; and an electronic system configured to monitor the photonic degradation of the solar cell from the photoluminescence measurement, wherein the electronic system is configured to characterize a solar cell based on the monitoring.

2. The solar cell testing apparatus of claim 1, wherein the detector is configured to measure photoluminescence induced from the applied light from the back side of the solar cell.

3. The solar cell testing apparatus of claim 1, wherein the narrowband light source is a laser or a light emitting diode (LED).

4. The solar cell testing apparatus of claim 1, wherein light from the narrowband light source and the measured photoluminescence are at least partially co-axial.

5. The solar cell testing apparatus of claim 1, further comprising a dichroic mirror to separate between the light from the narrowband light source and the measured photoluminescence.

6. The solar cell testing apparatus of claim 1, wherein the narrowband light source is an ultraviolet (UV) light source.

7. A solar cell testing apparatus, comprising:

a narrowband light source configured to induce photonic degradation to a solar cell, wherein the inducing includes applying light to the solar cell;

a detector configured to measure photoluminescence induced from the applied light; and an electronic system configured to monitor the photonic degradation of the solar cell from the photoluminescence measurement, wherein the electronic system is configured to quantify or qualify a solar cell based on the monitoring.

8. The solar cell testing apparatus of claim 7, wherein the narrowband light source is a laser or a light emitting diode (LED).

9. The solar cell testing apparatus of claim 7, wherein light from the narrowband light source and the measured photoluminescence are at least partially co-axial.

10. The solar cell testing apparatus of claim 7, further comprising a dichroic mirror to separate between the light from the narrowband light source and the measured photoluminescence.

11. The solar cell testing apparatus of claim 7, wherein the narrowband light source is an ultraviolet (UV) light source.

12. A method for testing a solar cell, the method comprising:

inducing photonic degradation, wherein the inducing includes applying light to the solar cell; and monitoring the photonic degradation of the solar cell based on a photoluminescence measurement, wherein the monitoring includes receiving a first photoluminescence measurement induced from the applied light and receiving a second photoluminescence measurement induced from the applied light during the first photoluminescence measurement.

13. The method of claim 12, wherein applying light to the solar cell comprises applying light having a photon energy above the bandgap energy of the semiconductor substrate of the solar cell.

14. The method of claim 12, wherein applying light to the solar cell comprises applying light from a narrowband light source.

15. The method of claim 14, wherein applying light from a narrowband light source to the solar cell comprises applying light from a narrowband light source having a wavelength in the range of 100-1000 nm to the solar cell.

16. The method of claim 12, wherein applying light to the solar cell comprises applying light to a passivation region of the solar cell.

17. The method of claim 12, wherein applying light to the solar cell comprises applying light to a location on a front side of the solar cell opposite a contact pad on back side of the solar cell.

18. The method of claim 12, further comprising:

inducing photonic degradation, wherein the inducing includes applying light to a plurality of locations of the solar cell; and monitoring the induced photonic degradation to the solar cell based on a photonic degradation map, wherein the monitoring includes receiving a plurality of photoluminescence measurements induced from the applied light and mapping the induced photonic degradation at the plurality of locations of the solar cell to the photonic degradation map.

19. The method of claim 12, wherein applying light to the solar cell comprises applying light to the solar cell for a duration in the range of 10 milliseconds-2 hours.

20. The method of claim 12, wherein applying light to the solar cell comprises applying light from a laser or a light emitting diode (LED) to the solar cell.

* * * * *